United States Patent [19]

Lacroix et al.

[11] Patent Number: 5,795,722
[45] Date of Patent: Aug. 18, 1998

[54] METHOD AND KIT FOR QUANTITATION AND NUCLEIC ACID SEQUENCING OF NUCLEIC ACID ANALYTES IN A SAMPLE

[75] Inventors: Jean-Michel Lacroix, Etobicoke; James M. Dunn, Scarborough, both of Canada

[73] Assignee: Visible Genetics Inc., Toronto, Canada

[21] Appl. No.: 819,912

[22] Filed: Mar. 18, 1997

[51] Int. Cl.$^6$ .................. C12Q 1/68; C12P 19/34
[52] U.S. Cl. ........................................ 435/6; 435/91.2
[58] Field of Search ................................ 435/6, 91.2

[56] References Cited

U.S. PATENT DOCUMENTS

| | | | |
|---|---|---|---|
| 4,358,535 | 11/1982 | Falkow et al. | 435/5 |
| 4,563,417 | 1/1986 | Albarella et al. | 435/6 |
| 4,683,195 | 7/1987 | Mullis et al. | 435/6 |
| 4,683,202 | 7/1987 | Mullis | 435/91 |
| 4,942,124 | 7/1990 | Church | 435/6 |
| 5,008,182 | 4/1991 | Shinsky et al. | 435/5 |
| 5,124,247 | 6/1992 | Ansorge | 435/6 |
| 5,171,534 | 12/1992 | Smith et al. | 422/82.05 |
| 5,176,995 | 1/1993 | Sninsky et al. | 435/6 |
| 5,219,727 | 6/1993 | Wang et al. | 435/6 |
| 5,283,171 | 2/1994 | Manos et al. | 435/5 |
| 5,403,707 | 4/1995 | Atwood et al. | 435/5 |
| 5,427,911 | 6/1995 | Ruano et al. | 435/6 |
| 5,453,355 | 9/1995 | Birkenmeyer et al. | 435/6 |

OTHER PUBLICATIONS

Chamberlain et al., "Detection of Gene Deletions Using Multiplex Polymerase Chain Reactions", *Meth. Molec. Biol.* 9: 299–312 (1991).

Ellison et al., "Detection of Mutations and Polymorphisms Using Fluorescence–Based Dideoxy Fingerprinting (F–ddF)", *Biotechniques* 17: 742–753 (1994).

Eisenstein, B.I., "The Polymerase Chain reaction", *New Engl. J. Med.* 322: 178–183 (1990).

Murakawa et al., "Direct Detection of HIV–1 RNA from AIDS and ARC Patient Samples", *DNA* 7: 287–295 (1988).

Ruano et al., "Coupled Amplification and Sequencing of Genomic DNA", *Proc. Nat'l Acad Sci (USA)* 88: 2815–2819 (1991).

Wiemann et al., "Simultaneous On–Line DNA Sequencing on Both Strands with Two Fluorescent Dyes", *Anal. Biochem* 224: 117–121 (1995).

*Primary Examiner*—Eggerton A. Campbell
*Attorney, Agent, or Firm*—Oppedahl & Larson

[57] ABSTRACT

A method for quantitative and qualitative analysis of a nucleic acid analyte in a sample suspected to contain the nucleic acid analyte first combines the sample with a control nucleic acid, and two primer pairs, a first primer pair effective to amplify a conserved region of the nucleic acid analyte if present in the sample to produce a conserved fragment having a first length and to amplify the control nucleic acid to produce a control fragment having a second length different from the first length, and a second primer pair effective to amplify a second region of the nucleic acid analyte to produce a sequencing fragment. One member of the first primer pair is labeled with a detectable label, and one member of the second primer pair may be labeled with a label such as biotin effective to permit capture of the primer. The combined mixture is then processed to amplify the sample and control nucleic acid using the first and second primer pairs to produce an amplification product mixture containing conserved fragments, sequencing fragments and control fragments when the nucleic acid analyte is present in the sample, and only control fragment when the nucleic acid analyte is not present in the sample. This product mixture is analyzed to determine the relative amounts of conserved fragments and control fragments in the amplification product mixture to quantify the amount of nucleic acid analyte in the sample and used as a starting point for a reaction to determine the sequence of the sequencing fragment.

27 Claims, 3 Drawing Sheets

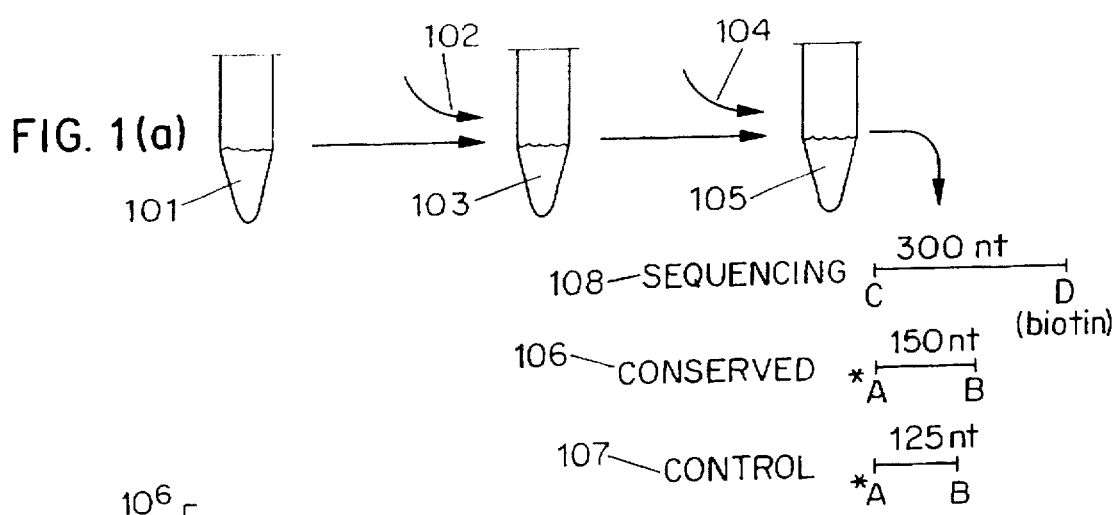
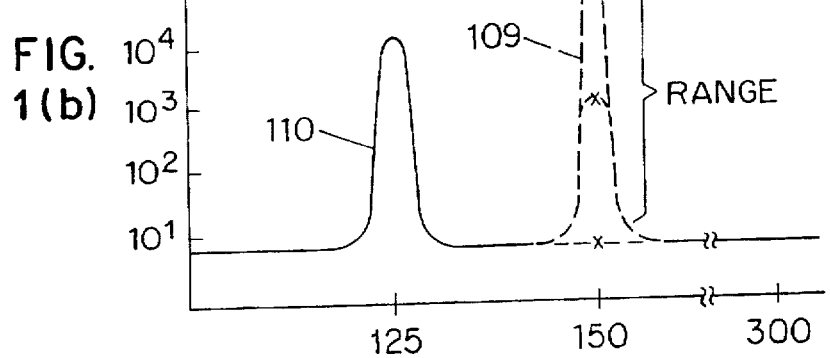
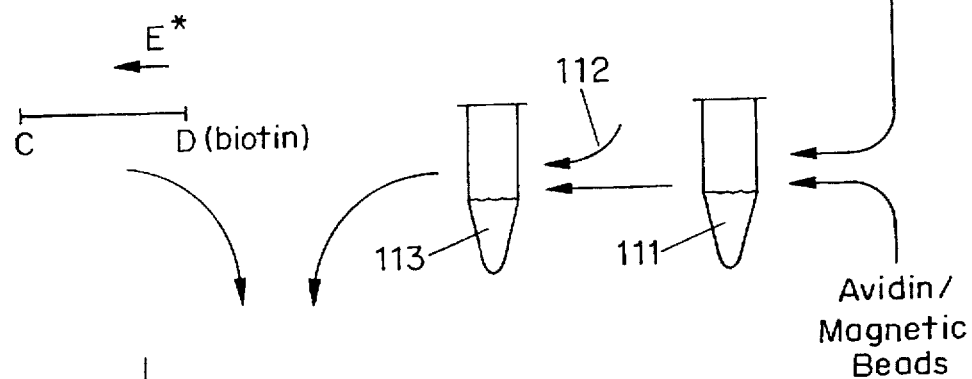
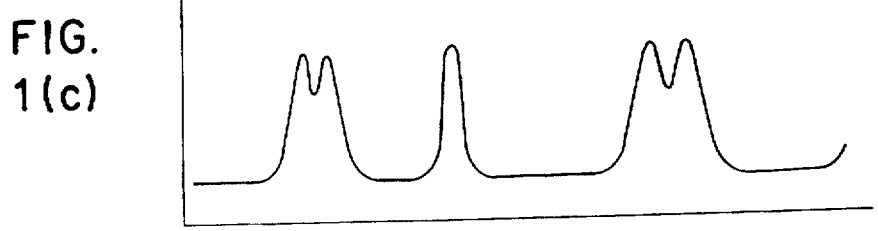
FIG. 1(a)
FIG. 1(b)
FIG. 1(c)

METHOD AND KIT FOR QUANTITATION AND NUCLEIC ACID SEQUENCING OF NUCLEIC ACID ANALYTES IN A SAMPLE

STATEMENT OF RELATED APPLICATIONS

This application is related to U.S. patent application Ser. No. 08/819.901, filed concurrently herewith, which related application is incorporated herein by reference.

BACKGROUND OF THE INVENTION

This invention relates to a method and kit for quantifying and partially sequencing a nucleic acid analyte that is present in a sample. The nucleic acid analyte may be from an infectious organism that is present in a patient sample.

Academic and commercial interest in nucleic acid diagnostics has, to date, focused on qualitative assays. This type of assay determines the presence or absence in a patient sample of a specific gene mutation or infectious pathogen. Molecular assays which achieve these goals are well known. Many rely on amplification techniques, known to those skilled in the art such as the polymerase chain reaction (PCR), NASBA or 3SR, with or without hybridization probing. Others such as Digene Hybrid Capture Assays (DiGene Diagnostics Inc.) do not require amplification prior to detection and are generally less sensitive. Assays have been developed for many infectious pathogens such as *Chlamydia trachomatis*, Human Immunodeficiency Virus Type 1 (HIV-1) and Type 2(HIV-2), and human papilloma virus (HPV). Some of these tests have been launched commercially by Roche Diagnostic Systems, Abbott Laboratories and others.

Quantitative assays of nucleic acid analytes also prove useful in diagnosis of a variety of medical disorders. For example, viral load in HIV infection may be correlated with increased risk of clinical progression of HIV disease (Mellors, J. W. et al. (1995). Quantitation of HIV-1 RNA in plasma predicts outcome after seroconversion. Ann. Intern. Med. 122: 573–579). While this example is best known, other quantitative applications also have clinical and commercial interest, such as quantitation of human papilloma virus in PAP smears. (Cuzick, J. et al. (1994) Type-specific human papillomavirus DNA in abnormal smears as a predictor of high-grade cervical intraepithelial neoplasia. Br. J. Cancer 69:167–171; Bavin P. J. et al. (1993) Use of semi-quantitative PCR for human papillomavirus DNA type 16 to identify women with high grade cervical disease in a population presenting with a mildly dyskaryotic smear report. Br. J. Cancer 67:602–605.)).

Notwithstanding their usefulness, quantitative assays of nucleic acid analytes have lagged behind in development. The delay may in part be attributed to technology barriers: Most instruments and methods provide inadequate dynamic range for measuring quantities, thus requiring labor intensive techniques such as multiple serial dilutions and repeat reactions. Further, until recently, PCR methods have been perceived as unreliable for quantitation due to the possibility of contamination and nonlinear enzyme kinetics.

The AMPLICOR HIV-1 MONITOR (Roche Molecular Systems) test is a quantitative molecular assay for HIV RNA levels in blood. The assay is performed on HIV-1 and a subset of HIV-2 RNA found in 200 uL of blood plasma. The plasma sample is lysed and RNA is reverse transcribed then amplified by PCR. The reaction products are quantified by a probe based photometric assay and compared to the levels of a control RNA of known quantity that is added to the plasma sample. The control RNA is reverse transcribed along with the sample RNA and co-amplified using the same amplification primers. Six serial dilutions are necessary to detect across the full range of detectable viral load: 400 copies to 750,000 copies per ml. The test requires that for samples over 750,000 copies, (over 2.2 million copies per ml have been detected) the original patient sample must be diluted. The AMPLICOR assay therefore quantifies across the full range of possible values by a series of multiple dilutions. The AMPLICOR assay does not determine which sub-type or sub-types of HIV-1 are present, and it does not establish if HIV-2 was amplified.

Other quantitative HIV assays have been reported. Some of these papers, incorporated herein by reference, include:

Mulder, J et al. Rapid and simple PCR assay for quantitation of human immunodeficiency virus type 1 RNA in plasma: Application to acute retroviral infection. J. Clin. Micro. 32:292–300

Dewar, R. L. et al, 1994 Application of branched DNA signal amplification to monitor human immunodeficiency virus type 1 burden in human plasma. J. Infect. Dis. 170:1172–1179 van Gemen, B. et al. 1993 Quantification of HIV-1-1 RNA in plasma using NASBA during HIV-1-1 primary infection. J. Vir. Meth. 43:177–188.

The possibility of integrating a quantitative nucleic acid assay with a qualitative assay, such as sequencing of the nucleic acid, has not been achieved or proposed by previous workers. The advantage of an integrated test, however, would be enormous. For example, not only could pathogen load be determined but also the exact serovar (or variety) of the pathogen could be determined. This would allow doctors and patients to know if treatments were effecting not only the quantity but also the variety of pathogen. In addition, a simplified assay would provide substantial economies of scale.

It is an object of the present invention to provide a method and kit for quantifying and determining the nucleic acid sequence of a nucleic acid analyte that is present in a patient sample.

SUMMARY OF THE INVENTION

These and other objects of the invention are achieved using a method for quantitative and qualitative analysis of a nucleic acid analyte in a sample suspected to contain the nucleic acid analyte, comprising the steps of:

(a) combining the sample with a control nucleic acid, and two primer pairs, a first primer pair effective to amplify a conserved region of the nucleic acid analyte if present in the sample to produce a conserved fragment having a first length and to amplify the control nucleic acid to produce a control fragment having a second length different from the first length, one member of the first primer pair being labeled with a detectable label, and a second primer pair effective to amplify a second region of the nucleic acid analyte to produce a sequencing fragment, one member of the second primer pair being labeled with a label effective to permit capture of the primer;

(b) amplifying the sample and control nucleic acid using the first and second primer pairs to produce an amplification product mixture containing conserved fragments, sequencing fragments and control fragments when the nucleic acid analyte is present in the sample, and only control fragment when the nucleic acid analyte is not present in the sample;

(c) analyzing the relative amounts of conserved fragments and control fragments in the amplification product mixture to quantify the amount of nucleic acid analyte in the sample; and (d) determining the sequence of the sequencing fragment in the amplification mixture to determine the qualitative characteristics of any nucleic acid analyte in the sample.

BRIEF DESCRIPTION OF THE DRAWINGS

FIGS. 1A–1C illustrate the method of the present invention;

DETAILED DESCRIPTION OF THE INVENTION

Figure 2:
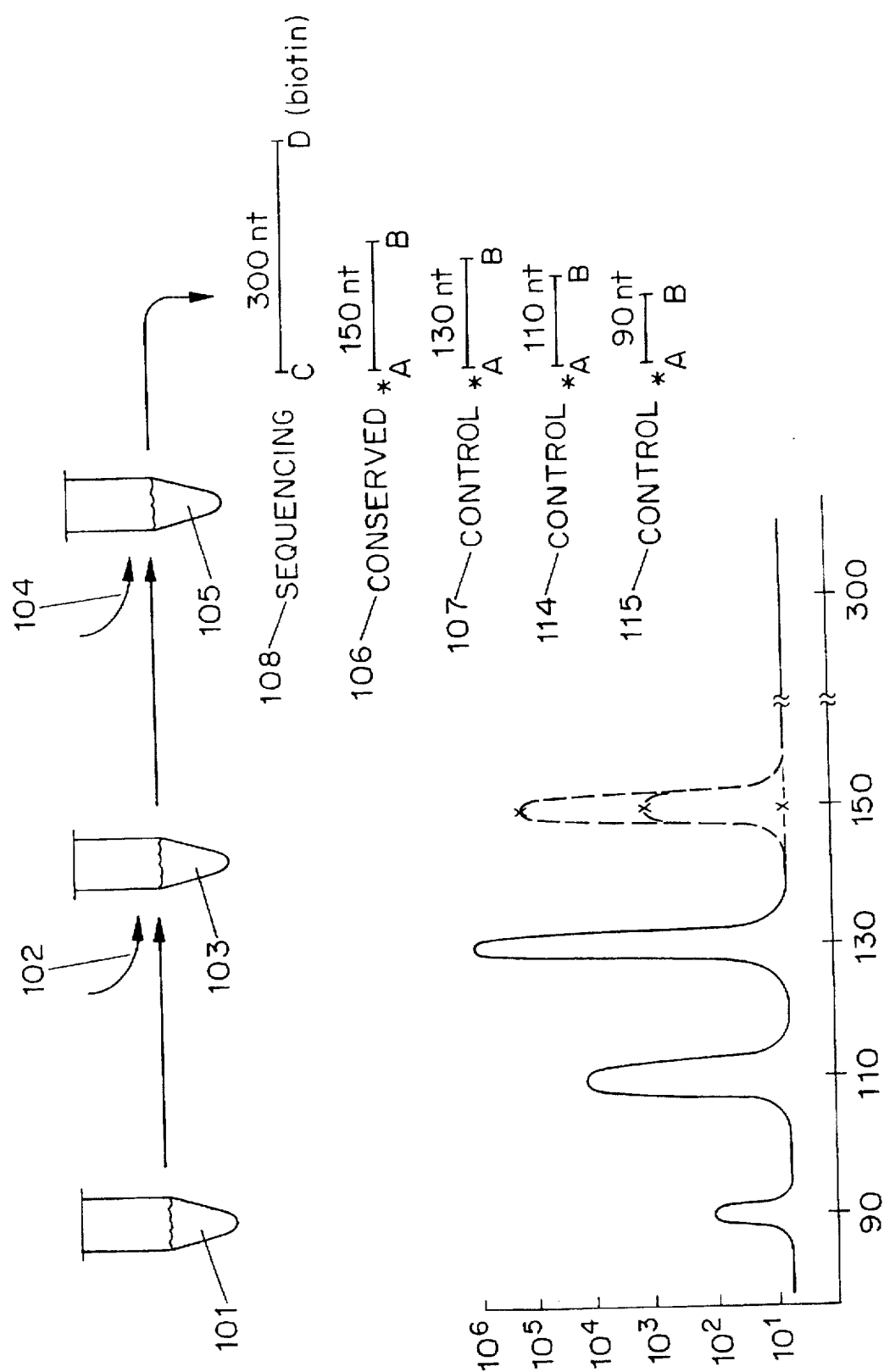
FIG. 2 illustrates an alternative embodiment of the method of the invention.

While this application generally uses terms relating to the method of the invention in their normal manner, the following definitions are provided to avoid ambiguity:

"Amplification" means the process of increasing the relative abundance of one or more specific genes or gene fragments in a reaction mixture with respect to the other genes. A method of amplification which is well known by those skilled in the art is the polymerase chain reaction (PCR) as described in U.S. Pat. Nos. 4,683,194, 4,683,195 and 4,683,202, which are incorporated herein by reference. The method is also explained in texts such as Current Protocols in Molecular Biology, (Eds. Ausubel, F. M. et al., (John Wiley & Sons; 1995)). The PCR process involves the use of pairs of primers, one for each complementary strand of the duplex DNA (wherein the coding strand is referred to as the "sense strand" and its complementary strand is referred to as the "anti-sense strand), that will hybridize at sites located on either side of a region of interest in a gene. Chain extension polymerization is then carried out in repetitive cycles to increase the number of copies of the region of interest exponentially. The amplified polynucleotide may be used as the template for a sequencing reaction. Gelfand et al. have described a thermostable enzyme, "Taq polymerase", derived from the organism *Thermus aquaticus*, which is useful in this amplification process (see U.S. Pat. Nos. 4,889,818; 5,352,600; and 5,079,352 which are incorporated herein by reference). Alternative amplification techniques such as NASBA, 3SR, Qb Replicase, and Branched Chain Amplification are known and available to persons skilled in the art.

"Patient sample" means a sample collected from a patient which may contain a nucleic acid analyte such as an infectious pathogen. Patient samples include but are not limited to blood samples, tissue samples, biopsy samples, excretions and secretions such as urine, feces or oral or genital mucosal swabs.

"Primer" means a polynucleotide of length 5–50 nucleotides which can serve to initiate a chain extension reaction. A "primer pair" is a pair of primers which specifically hybridize to sense (coding) and antisense (non-coding) strands of polynucleotide to permit amplification of the region lying between the primers of the pair.

"Reverse transcription" is the process of generating a DNA complement to an RNA molecule, and is generally accomplished with the use of a reverse transcriptase enzyme. A primer may be used to initiate polymerization; this primer may be one of a primer pair later used for PCR amplification. The RNA molecule is then separated from the copied DNA ("cDNA") or degraded by an RNAse H activity of an enzyme thus allowing the second strand of cDNA to be generated by a template dependent DNA polymerase. This method is disclosed in Units 3.7 and 15.4 of Current Protocols in Molecular Biology, Eds. Ausubel, F. M. et al, (John Wiley & Sons; 1995) which are incorporated herein by reference.

"Sequencing" or "DNA Sequencing" means the determination of the order of nucleotides in at least a part of a gene. A well known method of sequencing is the "chain termination" method first described by Sanger et al., PNAS (USA) 74(12): 5463–5467 (1977) and detailed in SEQUENAS™ 2.0 product literature (Amersham Life Sciences, Cleveland) and more recently elaborated in European Patent EP-B1-655506 all incorporated herein by reference. Basically, in this process, DNA to be sequenced is isolated, rendered single stranded, and placed into four vessels. In each vessel are the necessary components to replicate the DNA strand, which include a template-dependent DNA polymerase, a short primer molecule complementary to the initiation site of sequencing of the DNA to be sequenced and deoxyribonucleotide triphosphates for each of the bases A, C, G and T, in a buffer conducive to hybridization between the primer and the DNA to be sequenced and chain extension of the hybridized primer. In addition, each vessel contains a small quantity of one type of dideoxynucleotide triphosphate, e.g. dideoxyadenosine triphosphate ("ddA"), dideoxyguanosine triphosphate ("ddG"), dideoxycytosine triphosphate ("ddC"), dideoxythymidine triphosphate ("ddT"). In each vessel, each piece of the isolated DNA is hybridized with a primer. The primers are then extended, one base at a time to form a new nucleic acid polymer complementary to the template DNA. When a dideoxynucleotide is incorporated into the extending polymer, the polymer is prevented from further extension. Accordingly, in each vessel, a set of extended polymers of specific lengths are formed which are indicative of the positions of the nucleotide corresponding to the dideoxynucleotide in that vessel. These sets of polymers are then evaluated using gel electrophoresis to determine the sequence.

"Single Track Sequencing" means the method disclosed in U.S. patent application 08/577,858, assigned to the assignee of the instant invention and incorporated herein by reference. In Single Track Sequencing the positions of only one (or less than 4) nucleotide(s) of a target sequence is determined. Single Track Sequencing provides a finger-print or bar-code of the target sequence that may be sufficient to distinguish it from all other known varieties of the sequence. Throughput is increased by reducing the number of reactions and electrophoresis runs required to identify a sequence.

"Specific hybridization" means hybridization of an oligonucleotide to its exact complement, or a complement that is sufficiently similar that hybridization may occur in conditions that are of intermediate stringency.

"Target sequence" means the nucleic acid sequence that is the target of investigation. In PCR amplifications, the target sequence is bounded by and includes the sites of specific hybridization of the primer pair.

The present invention relates to a method and kit for quantifying and determining the nucleic acid sequence of a nucleic acid analyte that is present in a patient sample. This integrated test simplifies a series of laboratory tasks and provides physicians with better information about a patient's condition than previously described tests.

The general format of the method of the invention is illustrated in FIGS. 1A–1C. Total nucleic acids (DNA or RNA) 101 are prepared from a known amount of patient sample. The preparation 101 is mixed with a control nucleic acid 102 of known quantity to create a reaction pre-mixture 103. The pre-mixture 103 is treated with reagents 104 to create an amplification reaction mixture 105 if the sample is DNA, or if the preparation is RNA, reagents 104 are combined to create a combined reverse transcription and amplification reaction mixture 105. In either case, two pairs of amplification primers A, B and C, D are added to the amplification mixture 105.

The first primer pair (A, B) specifically hybridizes with the sense and antisense strands of a conserved region of the nucleic acid analyte and the control nucleic acid 102. One primer of the first pair (A, B) is conjugated at its 5'-end to a detectable label, such as a fluorescent label. The second primer pair (C, D) specifically hybridizes with the sense and antisense strands of a second distinct region of the nucleic acid analyte that is separate and distinct from the conserved region and suitable for typing by sequence analysis. One primer of the second pair (C, D) is conjugated at its 5'-end to biotin, or a similar label which permits physical capture of the primer.

When the amplification reagents 104 are added, and the resulting reaction mixture 105 is thermally cycled for amplification, three amplified reaction products are generated if the nucleic acid analyte is present in the patient sample. The two amplified reaction products expected from the first primer pair are i) a fragment 106 of fixed length from a region of the analyte that is highly conserved among all varieties or sub-types of the pathogen (the "conserved fragment"); and ii) a fragment 107 of a different length that is generated from the control nucleic acid (the "control fragment"). These two fragments are detectably labeled. The amplification product of the second primer pair extends across a region of high variability or clinical relevance among varieties or subtypes of the pathogen (the "sequencing fragment"). This fragment 108 is generally longer than the other two, and it is labeled with biotin or similar label which permits the physical capture of the sequencing fragment.

Quantitation is performed by loading part of the reaction mixture on an automated fluorescence detection electrophoresis instrument that has a dynamic range broad enough to include the quantitative range of measurements desired. Such an instrument is disclosed in U.S. patent application No. 08/353,932 now U.S. Pat. No. 5,710,628 and PCT patent application No. PCT/US95/15951, which are incorporated herein by reference and embodied in the MicroGene Blaster Automated DNA Sequencer (Visible Genetics Inc., Toronto). An improved version of this instrument is disclosed in U.S. patent application 08/819,910 No.VGEN.P-041) filed herewith. The peaks 109, 110 corresponding to conserved and control fragments 106, 107 are quantified by measuring the area under each peak of the output signal (FIG. 1B). Because the control fragment is added in known amount, the amount of nucleic acid in the original patient sample can be calculated by extrapolation. The sequencing fragment is not detected at this step.

The next step, sequencing of the sequencing fragment of the nucleic acid analyte, is achieved as follows when the nucleic acid analyte is detected in the quantification step. The remaining part of the reaction mixture (or a portion thereof) is passed over a solid support such as avidin coated-magnetic beads to capture the biotin-labeled sequencing fragment 108 from the remainder of the mixture 111. After washing, the sequencing fragment 108 is treated with reagents 112, including labeled sequencing primer E to form reaction mixture 113. Reaction mixture 113 is exposed to conditions suitable for DNA or RNA sequencing. Sequencing methods such as Cycle Sequencing as disclosed in European Patent No. 655,506, which is incorporated herein by reference, or CLIP™ Sequencing using THERMOSEQUENASE™ or similar enzymes as disclosed in U.S. patent applications Nos. 08/640,672 and 08/684,498, both of which are incorporated herein by reference, are preferred. In addition, the method may employ Single Track Sequencing to provide a finger-print or bar-code identity of the target sequence (FIG. 1C). Once the identity of pathogen variety, or mixture of varieties, is determined, it is reported to the patient file along with the quantitative data previously determined.

Because the sequencing fragment is amplified in the original amplification reaction, a separate amplification need not be performed, saving time and effort to reach the desired result. Further, sequencing can serve as an additional control for the quantitative assay. Results can be reported rapidly and accurately.

The method of the invention can be applied to samples containing either a DNA or an RNA nucleic acid analyte. Thus, the method is conveniently applied to diagnosis of infectious pathogens such as HIV-1and -2, HPV or C. trachomatis The selection of target sequences to be analyzed is an important aspect of the method. The fragment for quantitation (the "conserved fragment") is selected to be reliably amplified in all (or at least substantially all) varieties or sub-types of the nucleic acid analyte. For this reason the target sequence, and more specifically the primer hybridization sites at the ends of the target sequence, are selected to be from a region of the target sequence that is highly conserved among all varieties or sub-types. In addition these sequences are relatively short (i.e., 50 to 250 nucleotides) to ensure that chain extension reactions are reliably completed.

The control nucleic acid 102 is either RNA or DNA, corresponding to the nature of the nucleic acid analyte. The control nucleic acid is preferably amplified by the same primers used to produce the conserved fragment. This is to ensure that the parameters of the control reaction reflect the test reaction as closely as possible. A preferred control nucleic acid is a polynucleotide having a length of 50 to 2000 nucleotides that includes a modified copy of the "conserved fragment" that generates a significantly different sized reaction product when amplified (the "control fragment"). By "significantly different" it is intended that 1 nt difference may amount to a significant difference if the control fragment reaction product can be distinguished from the conserved fragment by the detection means. More likely, for detection by electrophoresis, the significant difference is an addition or deletion of 5–50 nt, preferably about 20 nt. Preferably the addition or deletion of nucleotides takes place away from the primer hybridization sites so as not to influence the key step of primer hybridization. The composition of deleted or added nucleotides is preferably designed to not influence the overall ratios of nucleotides in the conserved fragment, and no new secondary structures are added or removed. Workers skilled in the art are familiar with these and other methods of creating a control fragment that is similar in relevant features to the test sample nucleic acid.

A supply of control RNA can be generated by cloning the "control fragment" into an RNA transcription vector and generating large amounts of RNA in a transcription system. See: Current Protocols in Molecular Biology, (Eds. Ausubel, F. M. et al., (John Wiley & Sons; 1995)). Suitable control DNA can be generated by cloning the control fragment into a plasmid, generating a supply of the plasmid DNA and then linearizing the plasmid prior to adding it to the sample.

An alternative approach for the incorporation of the control nucleic acid is shown in FIG. 2. In this case, a plurality of control nucleic acids are utilized which amplify with the same primer pair to generate a plurality of control fragments 107, 114, 115. Each of the control nucleic acids has the features of the preferred control nucleic acids listed above, but produces a control fragment having a different length. Each control nucleic acid is added in different amounts to the patient sample DNA, corresponding to the dynamic range of possible target sequence amounts. For example, where HIV-1 levels are detected across the range of 40 to 4×10$^6$ copies per ml, control nucleic acids could be added representing 400 copies, 40,000 copies and 4,000,000 copies per ml thus providing an extended range of control levels from which to extrapolate the patient sample amount.

Selection of the "sequencing fragment" turns on somewhat different considerations from the control and conserved fragments. First, the sequencing fragment is preferably sufficiently remote from the conserved fragment within the target sequence that amplification of one does not hinder amplification of the other. Second, the sequencing fragment is selected to give information that is clinically relevant about the variety or sub-type of the organism.

The specific conserved fragments and sequencing fragments produced in an assay will, of course, vary depending on the nucleic acid analyte, and will frequently coincide with fragments generated in the course of other types of diagnostic assays for the same analyte. Primers may also be selected and designed through the use of computer programs such as OLIGO™ (National Biosciences Inc., Plymouth, Minn.). It will be appreciated by persons skilled in the art that primers tend to be idiosyncratic, and the primers that might be reasonably expected to work are often found to be unsuitable. Thus, some trial and error testing may be required to identify optimized primer pairs, based upon established principles for primer design and selection such as those disclosed in:

Breslauer et al. "Predicting DNA duplex stability from base sequence" PNAS (USA) 83: 3746–3750 (1986);

Rylchik, W. "Selection of Primers for Polymerase Chain Reaction" in Methods in Molecular Biology, Vol. 15: PCR Protocols: Current Methods and Applications, White, B. A. ed., Humana Press, Totowa, N.J., 1993.

Edwards et al. "Multiplex PCR" in PCR Primer: A Laboratory Manual eds. Diffenbach et al., CSHL Press; Plainview, N.Y., 1995.

To exemplify the selection of suitable target sequences and suitable primers, several specific nucleic acid analytes are discussed below, and in the Examples. These specific examples are provided as examples, and are not intended to limit the scope of the invention.

For HIV-1, a suitable conserved region lies within the HIV gag genes. The gag region encodes the group specific antigens or core structural proteins of the HIV virion. The HIV gag genes are generally about 1500 nucleotides in length and are located at the approximate positions 789–2290 of the HIV genome. A fragment of this region may be PCR amplified using the primers SK462 and SK 431.

|SEQ ID No.: 1|
SK462 AGTTGGAGGA CATCAAGCAG CCATGCAAAT
|SEQ ID No.: 2|
SK431 TGCTATGTCA GTTCCCCTTG GTTCTCT

These primers will generate a 142 nt fragment of the gag gene from a cDNA of all HIV-1sub-types and a subset of HIV-2subtypes. Amplification conditions are standard ones known in the art, and described in Kwok, S. and Sninsky J. J. PCR Detection of Human Immunodeficiency Virus Type 1Proviral DNA Sequences. Diagnostic Molecular Microbiology (Eds. Persing, Smith et al.) (Am. Soc. Micro., 1993) Chp. 2.1 p309–315.

A suitable sequencing fragment for HIV-1spans certain codons of the protease gene that are involved in protease inhibitor resistance (codons 46, 48, 54, 63 82 84 and 90). Not all varieties have these mutations. Sequence information from sequencing fragment should determine whether these mutations are present or not. A suitable sequencing fragment encompassing the relevant codons of the protease gene can be generated using the following primers:

PR211  ATCACTCTTT GGCAACGACC         |SEQ ID NO: 3|
or
PR281  CAGGAGCAGA TGATACAGTA TTAG    |SEQ ID NO: 4|
and
PR526: CCATTCCTGG CTTTAATTTT ACTGG   |SEQ ID NO: 5|

PR211–PR526 creates a sequencing fragment of maximum size 340 bp spanning nucleotides 6–334. PR281–PR526 creates a sequencing fragment of maximum size 270 bp spanning nucleotides 76–334. Other suitable sequencing fragments can be generated for other clinically relevant genes of HIV-1, such as the reverse transcriptase gene.

The method of the invention can be applied to HIV-1, and other RNA viruses by direct application to viral RNA, or it can be performed on corresponding cDNA or proviral DNA which has been integrated in the genome of a host cell.

By way of the further example, quantification and sequence-based serotyping of *C trachomatis* can be achieved using primers which produce a conserved fragment taken from the cryptic plasmid of *C. trachomatis* which is recognized as a suitably specific target sequence or detection purposes, but which is not known to vary from strain to strain. Suitable primers for this purpose are:

KL1: TCCGGAGCGA GTTACGAAGA   |SEQ ID NO: 6|
KL2: ATTCAATGCC CGGGATTGGT   |SEQ ID NO: 7| which were used as amplification primers in Mahony et al., "Confirmatory polymerase chain reaction testing for *Chlamydia trachomatis* in first void urine from asymptomatic and symptomatic men" J. Clin Microbiol. 30:2241–2245 (1992); or CT1431F GTGCATAAAC TTCTGAGGAT   |SEQ ID NO: 8|
CT1548R GTAAACGCTC CTCTGAAGTC   |SEQ ID NO: 7|

A suitable strain specific target sequence for *C. trachomatis* is the omp1 (outer membrane protein) gene which has at least 4 variable sequence ("VS") domains that may be used to distinguish among the 15 known genotypes of *C. trachomatis* (Yuan, Y et al. "Nucleotide and Deduced Amino Acid Sequences for the Four Variable Domains of the Major Outer Membrane Proteins of the 15 *Chlamydia trachomatis* Serovars" Infect. Immun. 57 1040–1049 (1989)). The following oligonucleotide primers may be employed for production of sequencing fragments taken from the VS1/VS2 or VS3/VS4 domains:

|SEQ ID NO. 10|
OMP314A TGACTTTGTT TTCGACCGYG TTTT
|SEQ ID NO. 11|
OMP711  CATCCACATT CCCASARAGC TGC

-continued

For VS1/VS2:  [SEQ. ID NO. 12]
MF21    CCGACCGCGT CTTGAAAACA GATGT
MB22    CACCCACATT CCCAGAGAGC T  [SEQ. ID NO. 13]

For VS3/VS4
MVF3    CGTGCAGCTT TGTGGGAATG T  [SEQ. ID NO. 14]
                                  [SEQ. ID NO. 15]
MB4     CTAGATTTCA TCTTGTTCAA TTGC
Mahoney et al., supra.

Primers which will amplify the target sequences of the nucleic acid analyte to produce conserved fragments, control fragment and sequencing fragments may be synthesized by well known phosphoramidite chemistry. One of the amplification primers used to produce the conserved and control fragments is preferably labeled with a detectable label that can be detected on an instrument with a wide dynamic range. Suitable detectable labels include radioisotopes $^{32}$P, $^{33}$P, or $^{35}$S, biotin moieties that may be conjugated to avidin-linked chromogenic moieties, or fluorescent moieties. A preferred label for detection on the Visible Genetics MICROGENE BLASTER™ is Cy5.5 (Amersham Life Sciences) conjugated to the 5'-end of one of the primers. Label conjugation may be achieved using standard techniques such as dye-ester conjugation with HPLC purification.

As noted above, one of the primers used to amplify the sequencing fragment is preferably conjugated at its 5'-end to biotin or a similar moiety which will permit selective capture of primer. A biotin label allows the sequencing fragment to be purified from the original amplification mixture using avidin coated magnetic beads such as DYNA-BEADS M-280 (Dynal, Oslo, Norway). Purification can improve the results of sequencing reactions but it is not always necessary, depending on the design of the protocol.

The primer pairs selected for amplification of the conserved and sequencing fragments are combined with a sample containing the nucleic acid analyte in a form accessible for amplification to form amplification reaction mixture. In the case, of an RNA analyte, amplification of the sample must be proceeded by reverse transcription to create a DNA sequencing template. This step is conveniently achieved by the addition of the thermostable DNA polymerase isolated from *Thermus thermophilus*. This enzyme has reverse transcriptase activity in the presence of $Mn^{2+}$ and DNA polymerase activity under thermal processing conditions. (Myers, T. W. and D. H. Gelfand. 1991. Reverse transcription and DNA amplification by a *Thermus thermophilus* DNA polymerase. Biochemistry 30:7661–7666). Amplification primers are added to the reaction mixture, with chain extension reagents. In the first reduced temperature step, one primer hybridizes to the RNA and the primer is extended to generate one strand of cDNA. In the second step of high temperature thermal processing, the cDNA is copied by the reverse primer, thus generating a double stranded molecule, and leading to an exponential increase in cDNA amounts after repeated cycles.

The amplification reaction mixture is processed through a plurality of thermal cycles, generally 10 to 40 cycles, to produce an amplified product mixture containing conserved, control and sequencing fragments. The amplified product mixture is then loaded onto an electrophoresis gel and evaluated for the presence of detectable control and conserved fragments.

Some of the benefits of the present invention, notably the simplification that results from the simultaneous production of the conserved fragment and the sequencing fragment can be achieved regardless of the nature of the instrument on which the evaluation is performed. Thus, on an instrument with low or modest dynamic range, serial dilutions of the amplified product mixture can be loaded onto the electrophoresis gel for evaluation. Preferably, however, the analysis is performed on an instrument having a dynamic range that permits the detection of conserved and control fragments at concentrations spanning several (i.e. 3 or more) orders of magnitude.

The specific configuration of the instrument employed to measure the amount of conserved fragment and control fragment(s) on an electrophoresis gel will depend on the nature of the detectable labels employed, and persons skilled in the art will have no difficulty matching any given type of label with a compatible instrument. The preferred type of label affixed to the conserved and control fragments is a fluorescent label. Thus, instruments which are suitable for detection of fluorescent conserved and control fragments are discussed herein in detail.

As noted above, a substantial challenge in quantifying the amount of nucleic acid analyte in a sample is the broad range of concentrations which may be encountered, and the substantial differences which may exist between the concentration of the nucleic acid analyte and the concentration of the control nucleic acid. Since fluorescence intensity is generally (absent issues such as quenching, saturation of the fluorescent reagent or photochemical reaction) directly proportional to the amount of fluorescent compound present and the number of input photons of appropriate energy for excitation in the excitation beam, a simple linear calibration curve over a several serial dilutions of the sample can be used to determine the amount of nucleic acid in the original sample even in an instrument which lacks the dynamic range to accommodate substantial concentration differences between sample and control.

Preferably, however, the measurements are made with an instrument such as a MICROGENE BLASTER electrophoresis and DNA sequencing apparatus (Visible Genetics Inc., Toronto, Canada). The MICROGENE BLASTER has a dynamic range extending over about three orders of magnitude, since the instrument can detect a band when from about 1 attomol ($10^{-18}$) to about 1 femtomol ($10^{-15}$) of a single species of DNA loaded per well. Thus, the instrument makes it possible to eliminate serial dilutions from the laboratory protocol, and perform a single reaction, with a single control nucleic acid or set of control nucleic acids for each patient sample.

The structure of the current MICROGENE BLASTER apparatus is described in U.S. patent application No. 08/353, 932 now U.S. Pat. No. 5,710,628 and PCT patent application No. PCT/US95/15951. Thus, a suitable apparatus is an apparatus for electrophoretic separation and detection of a plurality of samples, each labeled with a fluorophore and loaded into a lane of an electrophoresis gel, comprising:

(a) a housing adapted to receive an electrophoresis gel holder containing an electrophoresis gel loaded with the samples;

(b) a laser diode excitation source for providing an incident beam of coherent radiation of a frequency suitable for excitation of the fluorophore;

(c) a spot array generation grating for dividing the incident beam of coherent radiation into a plurality of excitation beamlets of the frequency suitable for excitation of the fluorophore and directing each excitation beamlet to an excitation/detection site on a different lane of the electrophoresis gel; and (d) an array of detectors aligned with the excitation/detection sites for collecting fluorescent emissions. The collected emissions are preferably processed using a computer program such as GENEOBJECTS™ signal processing an evaluation software (Visible Genetics Inc.), although the fundamental simplicity of the peak pattern detected (i.e., as few as two peaks in the case of a conserved fragment and a single control fragment) makes the use of very sophisticated peak identification algorithms generally unnecessary.

Although the MICROGENE BLASTER apparatus provides high dynamic range and is fully suitable for use in the invention, certain improvements can further increase the dynamic range of the instrument. Thus, a preferred high-dynamic range instrument for use in practicing the method of the invention is of the type described in concurrently filed U.S. patent application No. 08/819,910. This instrument incorporates one or more of the following approaches for increasing the dynamic range of the instrument:

(1) modulation of signal integration periods can be employed so that large signals are totaled at short time intervals and smaller signals are totaled at longer time intervals. This approach is disclosed in U.S. patent application No. 08/452,719 which is incorporated herein by reference.

(2) the instrument can incorporate a beam splitter which produces a high intensity beam and a low intensity beam from each excitation/detection site and detects the two beams separately. When the signal strength is high, the low intensity beam will generally be below the saturation threshold of the detector, while when the signal strength is low, the high intensity beam is generally above the detection threshold of the detector.

(3) modulation of the intensity of the excitation beam can be used improve the dynamic range of the instrument. Thus, for example, is a 20 mW laser diode (which has a variable output of 1–20 mW) is used at power levels varying in a stepwise fashion from 1 mW at the low end to 20 mW at the high end, measurements can be taken during either the low power window and the high power window, depending on the strength of the signal.

If a peak is detected in the quantitation stage indicating the presence of the nucleic acid analyte in the sample, the next step in the method is the determination of the sequence of the sequencing fragment. Sequencing reactions may be performed by any means known in the art. A preferred method is to perform cycle sequencing using a labeled primer that specifically hybridizes to the sequencing fragment only, in the presence of chain extension reagents, one chain terminating reagent (such as ddTTP) and THERMOSEQUENASE (™) enzyme (Amersham Life Sciences, Cleveland). The sequencing primer may be the same as one of the amplification primers, or it may be "nested", i.e. specifically hybridizing to a site not at the end of the fragment. The fluorescent label preferred for use on the Visible Genetics MicroGene Blaster is Cy5.5. If different instruments are used, different labels may be employed.

An alternative method for sequencing is to employ the CLIP™ sequencing technique, disclosed in U.S. patent applications Ser. Nos. 08/640,672 and 08/684,498 assigned to the assignee of the present application and incorporated herein by reference. In this method two primers similar to amplification primers are employed in a chain termination sequencing reaction. This generates chain terminated fragments from both strands of the template. Each primer is given a different detectable label so that when the results are run on an automated fluorescence sequencer with multi-dye detectors, both strands can be sequenced with a minimum number of steps.

Single Track Sequencing, the method disclosed in U.S. patent application 08/577,858 is also available to facilitate the method. In Single Track Sequencing the positions of only one (or less than 4) nucleotide(s) of a target sequence are determined. Single Track Sequencing provides a fingerprint or bar-code of the target sequence that may be sufficient to distinguish it from all other known varieties of the sequence. Throughput is increased by reducing the number of reactions and electrophoresis runs required to identify a sequence.

Figure 3:
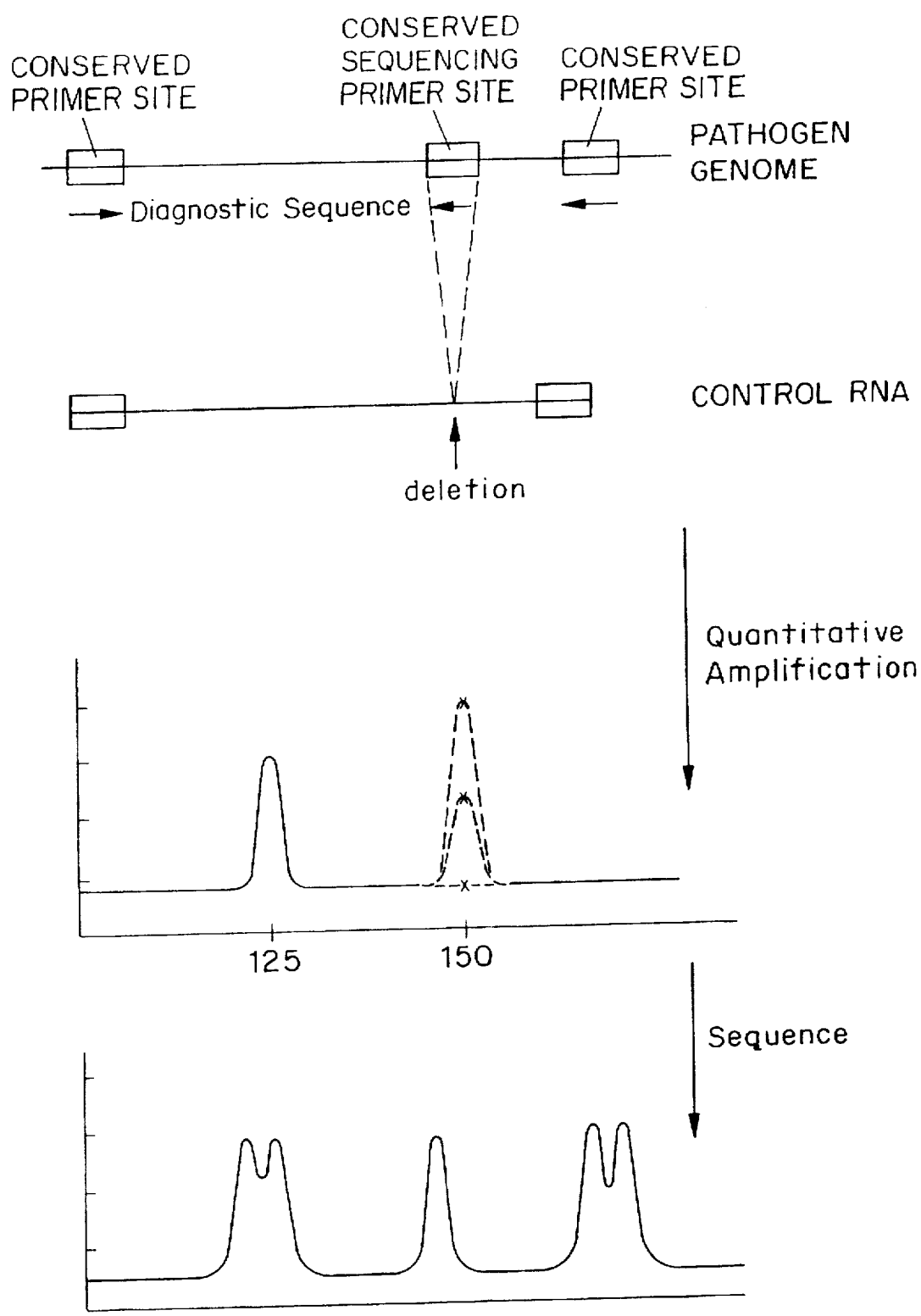
FIG. 3 illustrates the method of the present invention.

It is conceivable that the sequencing fragment and the conserved fragment could be the same fragment in certain organisms. This would be the case if the diagnostically relevant gene were bounded by highly conserved primer hybridization sites as illustrated in FIG. 3. In this case, the amplification step is performed with only a first labeled primer pair. One primer has a first detectable label, the other is biotinylated. The quantitative amplification is performed and measured. After the amplification, the remaining reaction mixture is converted to a sequencing reaction mixture by purification of the template strand (if necessary), and the addition of a sequencing primer, a chain-terminating agent, suitable buffers and reagents and a sequencing enzyme. The sequencing primer is given a different label from the first primer pair so that sequencing reaction products are distinguishable.

FIG. 3 also illustrates that the control fragment must be designed so as not to contain a site for specific hybridization of the sequencing primer. This consideration suggests that a deletion could be engineered in the control fragment that corresponds to the sequencing primer hybridization site in the conserved fragment. This would ensure that no control fragment template would be sequenced.

The method of the present invention is conveniently practices with reagents provided in kit format, and such kits form an aspect of the present invention. Such a kit comprises, in packaged combination, a control nucleic acid that is structurally related to a conserved region of a target nucleic acid analyte, a first primer pair for amplification of the control nucleic and the conserved region, and a second primer pair for amplification of a second region of the nucleic acid analyte different from the first region. One member of the first primer pair is labeled with a detectable label, preferably a fluorescent label. One or both members of the second primer pair may be labeled with a capture moiety such a biotin which will facilitate separation of the amplification product of this primer pair from a reaction mixture. The kit may further include polymerase enzymes, buffers and sequencing reagents.

The invention will now be further exemplified with reference to the following, non-limiting examples.

EXAMPLE 1

Quantitation of serum HIV-1 levels is achieved according to the method of the invention as follows:

Blood serum is collected and prepared according to methods known in the art, with the exception that heparin is not to be used as an anti-coagulant because it inhibits PCR. EDTA is preferred (collection tube #6454 Becton-Dickinson). Plasma is separated from whole blood by centrifugation (600–1600×g for 20 mins) and transferred to a polypropylene tube. A preparation tube is prepared containing 200 ul of patient serum.

600 ul lysis reagent containing control RNA is added to the preparation tube. Control RNA is a 200–1000 nt RNA molecule containing a gag gene sequence (the "control fragment") corresponding to the conserved fragment but with a 20 nt internal deletion. The quantity added corresponds to an amount in the mid-log range of the possible sample values, approximately $4 \times 10^4$ copies per ml of serum.

13

(Since 200 ul of serum is used, $0.8 \times 10^4$ copies of RNA is added.) Lysis reagent includes Tris-HCl buffer, 68% guanidine thiocyanate, dithiothreitol and glycogen. Samples are vortexed and incubated a room temperature for 10 minutes. After 10 minutes, 800 ul of 100% isopropanol is added and vortexed.

Samples are centrifuged ($12,500 \times g$) for 15 minutes at room temperature. Supernatant is removed, and the sample is washed again in 70% ethanol.

RNA is resuspended in 400 ul TE buffer (10 mM Tris, 1 mM EDTA) containing carrier poly rA RNA. The sample is vortexed vigorously.

The following reagents are then added to a reaction tube.

|  | final amount/volume |
|---|---|
| patient sample/control RNA | 12.5 ul |
| nucleoside triphosphates (dATP, dCTP, dUTP, dGTP) | 2.5 mM each |
| A,B amplification primers | 4-8 pmol each |
| C,D amplification primers | 4-8 pmol each |
| Mn2+ reaction buffer (Roche Molecular Systems, Inc.) | 1X |
| Uracyl-N-glycosylase (Roche Molecular Systems, Inc.) | 0.1 U |
| Tth Polymerase (Roche Molecular Systems, Inc.) | 50 U |
| distilled H2O | remainder up to 25 ul |
| Total Volume: | 25 ul |
| A primer 5'-Fluorescent label for detection with MicroGene Blaster preferably Cy5.5 (Amersham Life Sciences, Cleveland). Cy5.5-5'-HIV one | |
| SK462 AGTTGGAGGA CATCAAGCAG CCATGCAAAT | [SEQ ID NO: 1] |
| B primer HIV gag2 | |
| SK431 TGCTATGTCA GTTCCCCTTG GTTCTCT | [SEQ ID NO: 2] |
| C primer 5' biotin label sequencing fragment | |
| PR211 ATCACTCTTT GGCAACGACC | [SEQ ID NO: 3] |
| or | |
| PR281 CAGGAGCAGA TGATACAGTA TTAG | [SEQ ID NO: 4] |
| D primer Sequencing fragment | |
| PR526: CCATTCCTGG CTTTAATTTT ACTGG | [SEQ ID NO: 5] |
| The reaction mixture is thermally processed according to the following schedule: | |
| 50° C./2 min | |
| 60° C./30 min | |
| Then 4 cycles of | |
| denaturation: | 95° C./10 sec |
| annealing: | 55° C./30 sec |
| extension: | 72° C./30 sec |
| Then 26 cycles of | |
| denaturation: | 90° C./16 sec |
| annealing: | 60° C./30 sec |
| extension: | 72° C./30 sec |

After a final denaturation of 95° C. for 30 seconds, the sample is left on ice. Quantitation is achieved by adding a portion (5 ul) of the reaction products to an equal volume of STOP/Loading buffer consisting of 100% formamide and a colored dye. 1.5 ul of final mixture is loaded on a MicroGene Blaster Automated DNA Sequencer (Visible Genetics Inc., Toronto).

The results are displayed on GeneObjects software, on a logarithmic grid. The area under the control fragment peak is measured. This is compared to the area under the conserved fragment peak. The amount of HIV mRNA in the original patient sample is extrapolated from a comparison of the two areas, based on knowledge of the amount of control RNA initially added.

14

EXAMPLE 2

The method of Example 1 can be modified to provide a series of amplification controls. In this case, the method of Example 1 is followed with the following changes.

The control RNA added prior to the lysis consists of three species. Each RNA is approximately the same size, 200–1000 nt, but the "control fragment" sequence between the primer hybridization sites have different sizes. Each of the different controls are added in different amounts. The first generates an amplification product of 90 bp and is added to correspond to 1000 copies per ml of serum. The second generates a 110 bp fragment and is present in $10^5$ copies. The third generates a 130 bp fragment and is present at $10^6$ copies. This range of amplifications provides an improved basis from which the original patient sample amounts can be determined.

EXAMPLE 3

The sequencing fragment is isolated from the remaining portion of the amplification reaction mixture obtained in Example 1 as follows.

10 ul of avidin coated magnetic beads such as Dynabeads M-280 (Dynal, Oslo, Norway; washed and prepared according to manufacturers instructions) are added to 10 ul of the remaining amplification reaction products and incubated for up to 1 hr at room temperature. The beads are isolated with a magnet and the supernatant is removed. The separated beads are then washed with 50 ul of 2× BW buffer (10 mM Tris, pH 7.5, 1 mM EDTA, 2M NaCl) followed by 50 ul of 1× TE buffer (10 mM Tris, 1 mM EDTA). After washing, the beads are resuspended in 10 ul of TE buffer.

EXAMPLE 4

Once the sequencing fragment is prepared, according to Example 3, the variety or sub-type of the pathogen can be determined by Single Track Sequencing.

A reaction mixture is prepared as follows:

3 ul bound beads 3 ul sequencing primer (30 ng total)

2 ul 13X sequencing buffer (260 mM Tris-HCL, pH 9.5, 39 mM $MgCl_2$)

2 ul Thermo Sequenase (Amersham Life Sciences, Cleveland) ((diluted 1:10 from stock to 3.2 U/ul)

3 ul distilled H2O.

Final Volume: 13 ul

The sequencing primer employed is the non-biotinylated primer of the sequencing template amplification reaction, but this time it is labeled with a detectable label. The preferred label for detection on the MicroGene Blaster is Cy5.5 linked to the 5' nucleotide of the primer.

PR526: CCATTCCTGG CTTTAATTTT ACTGG [SEQ ID NO: 5]

The reaction mixture is kept on ice. A single chain termination reaction mixture, in this case for the T nucleotide, is prepared by combining 750 uM of each of dATP, dCTP, dGTP and dTTP; and 2.5 uM of ddTTP. 3 ul of the termination reaction mix is place in a tube. 3 ul of the sequencing reaction mixture is added. An oil overlay is added and the single track reaction mixture is heated to 95° C. for 2 mins in a PTC-100 Programmable Thermal Controller (MJ Research, Inc.) or Robocycler Gradient 96 (Stratagene) before being thermally processed for 25 cycles (or fewer if found to be satisfactory) as follows:

Annealing: 50° C. for 10 Sec.
Extension: 70° C. for 30 Sec.
Denaturation: 95° C. for 30 Sec.

After a final extension at 70° C. for 5 min the sample is denatured at 95° C. for 30 secs and left on ice. The sample is mixed with 6 ul of STOP/Loading buffer containing 100% formamide and 5 mg/ml dye such as dextran blue.

1.5 ul of the mixture is loaded on a single lane of a MICROGENE BLASTER (Visible Genetics Inc., Toronto) and reaction products are separated by electrophoresis through a denaturing polyacrylamide gel. The reaction products are detected and presented with GENEOBJECTS software (Visible Genetics Inc., Toronto). The finger-print or bar-code of the reaction products is compared to all known varieties of the pathogen nucleic acid sequence. An exact match is sought. If only one match is found, that subtype or variety is positively identified. If the patient sample had mixed varieties the result may show a heterogenous mix. The members of the heterogenous mix and relative quantities may be determined.

EXAMPLE 5

Alternatively, once the sequencing fragment is prepared as in Example 3, the variety or sub-type of the pathogen can be determined using CLIP™ sequencing methodology. In this method the sequence of both the sense strand and antisense strand of the protease gene of HIV-1 may be obtained in a one step reaction as follows.

Combine the following materials and mix well:

|  | Concentration | Amount |
|---|---|---|
| Sequencing fragment DNA |  | 3 ul |
| PR211*Cy5.5 Primer | 10 uM | 0.5 ul |
| PR526*Cy5.0 Primer | 10 uM | 0.5 ul |
| diluted Thermosequenase Enzyme | 3.2 U/ul | 2 ul |

|  | Concentration | Amount |
|---|---|---|
| 13 X Reaction buffer |  | 2 ul |
| double distilled H2O |  | 5 ul |
| TOTAL VOLUME |  | 13.0 ul |

13X reaction buffer consists of Tris-HCL 260 mM pH 8.3, MgCl$_2$ 39 mM.
PR211     ATCACTCTTT GGCAACGACC          [SEQ ID NO: 3]
PR526:    CCATTCCTGG CTTTAATTTT ACTGG     [SEQ ID NO: 5]

Place 3 ul of mixture into each of 4 tubes. Heat tubes to 94° C. for 5 mins then reduce temperature to 85° C. Add and mix 3 ul of an 85° C. dNTP/ddNTP solution containing 0.75 mM each dNTP and 2.5 uM of a chain terminating nucleotide triphosphate (ddNTP) (use a different ddNTP in each of the 4 tubes).

Treat the mixture to 60 cycles of the following thermal cycling reactions: 94° C. for 10 sec, 62° C. for 15 sec, 70° C. for 1 min. Upon completion, treat the mixture for a final 5 min at 70° C. and then store at 4° C. until ready for loading. For viewing the reaction products, add an equal volume of stop/loading solution (95% formamide plus a colored dye). Take 1.5 ul and load in a single lane of a two dye MicroGene Blaster automated DNA sequencer (Visible Genetics Inc., Toronto).

The reaction products from the both labeled primers are detected on the MICROGENE BLASTER as two separate traces, and displayed on GENEOBJECTS Software.

The base-called results from each primer were compared to the known protease gene sequences of HIV-1 and -2 by GENELIBRARIAN (a component of GENEOBJECTS (Visible Genetics Inc., Toronto). The sub-type of HIV-1 or HIV-2 is determined, and the presence of drug resistance codons is determined. Once the sequence of the HIV sub-type(s) is determined, it is reported to the patient file along with the quantitation data.

The above examples are non-exclusive embodiments of the invention claimed below.

---

We claim:

1. A method for quantitative and qualitative analysis of a nucleic acid analyte in a sample suspected to contain the nucleic acid analyte, comprising the steps of:
(a) combining the sample with a control nucleic acid, and two primer pairs,
a first primer pair effective to amplify a conserved region of the nucleic acid analyte if present in the sample to produce a conserved fragment having a first length and to amplify the control nucleic acid to produce a control fragment having a second length different from the first length, one member of the first primer pair being labeled with a detectable label, and
a second primer pair effective to amplify a second region of the nucleic acid analyte to produce a sequencing fragment, one member of the second primer pair being labeled with a label effective to permit capture of the primer;

(b) amplifying the sample and control nucleic acid using the first and second primer pairs to produce an amplification product mixture containing conserved fragments, sequencing fragments and control fragments when the nucleic acid analyte is present in the sample, and only control fragment when the nucleic acid analyte is not present in the sample;

(c) analyzing the relative amounts of conserved fragments and control fragments in the amplification product mixture to quantify the amount of nucleic acid analyte in the sample; and (d) determining the sequence of the sequencing fragment in the amplification mixture to determine the qualitative characteristics of any nucleic acid analyte in the sample.

2. The method according to claim 1, wherein a plurality of control nucleic acids are added to the sample, each control nucleic acid producing a corresponding control fragment having a different length, and each control nucleic acid being added to the sample in different amounts.

3. The method according to claim 1, wherein at least a first and a second control nucleic acid are added to the sample, and the amounts of the first and second control nucleic acid differ by a factor of 10 or more.

4. The method according to claim 1, wherein the length of the conserved fragment differs from the length of the control fragment by at least 10 nucleotides.

5. The method according to claim 1, wherein the length of the conserved fragment differs from the length of the control fragment by at least 25 nucleotides.

6. The method according to claim 1, wherein the length of the conserved fragment differs from the length of the control fragment by at least 50 nucleotides.

7. The method according to claim 1, wherein the relative amounts of conserved fragments and control fragments are analyzed by separation of the fragments by gel electrophoresis and detection of the separated fragments.

8. The method according to claim 7, wherein the separation and detection of the separated fragments is performed on an instrument having a dynamic range of at least three orders of magnitude.

9. The method according to claim 7, wherein the separation and detection of the separated fragments is performed on an instrument having a dynamic range of at least three orders of magnitude.

10. The method according to claim 1, wherein the detectable label is a fluorescent label.

11. The method according to claim 1, wherein the label effective to permit capture of one member of the second primer pair is biotin.

12. The method according to claim 11, wherein the detectable label is a fluorescent label.

13. The method according to claim 12, wherein the relative amounts of conserved fragments and control fragments are analyzed by separation of the fragments by gel electrophoresis and detection of the separated fragments.

14. The method according to claim 13 wherein the separation and detection of the separated fragments is performed on an instrument having a dynamic range of at least three orders of magnitude.

15. The method according to claim 13, wherein the separation and detection of the separated fragments is performed on an instrument having a dynamic range of at least three orders of magnitude.

16. The method according to claim 1, wherein the nucleic acid analyte is HIV-1 RNA or corresponding cDNA or proviral DNA which is integrated into the genome of a host cell.

17. The method according to claim 16, wherein the first primer pair amplifies a conserved region within the gag genes of HIV-1.

18. The method according to claim 16, wherein the second primer pair amplifies a region within the protease gene of HIV-1.

19. The method according to claim 18, wherein the first primer pair amplifies a conserved region within the gag genes of HIV-1.

20. The method according to claim 1, wherein the first and second primer pairs are the same, and wherein one member of the pair has a detectable label and the other member of the pair has a label effective to permit capture of the primer.

21. The method according to claim 1, further comprising the step of capturing the sequencing fragment using the label effective to permit capture of one member of the second primer pair, thereby separating the sequencing fragment from the remainder of the amplification product mixture prior to sequencing the sequencing fragment.

22. The method according to claim 21, wherein the label effective to permit capture of one member of the second primer pair is biotin.

23. The method according to claim 1, wherein sequencing is performed on both the sense and antisense strands of the sequencing fragment using two species of distinctly labeled sequencing primers, said two species of sequencing primers each binding to a different one of the sense and antisense strands of the sequencing fragment.

24. The method according to claim 1, wherein the nucleic acid analyte is an RNA, further comprising the step of reverse transcribing the nucleic acid analyte prior to the amplification step.

25. A kit for quantitative and qualitative evaluation of a target nucleic acid analyte in a sample comprising, in packaged combination, (a) a control nucleic acid that is structurally related to a conserved region of the target nucleic acid analyte;

(b) a first primer pair for amplification of the control nucleic and the conserved region, one member of the first primer pair being labeled with a detectable label; and (c) a second primer pair for amplification of a second region of the nucleic acid analyte different from the first region.

26. The kit according to claim 25, wherein at least member of the second primer pair is labeled with a capture moiety to facilitate separation of the amplification product of this primer pair from a reaction mixture.

27. The kit according to claim 26, wherein the capture moiety to biotin.

* * * * *

UNITED STATES PATENT AND TRADEMARK OFFICE
CERTIFICATE OF CORRECTION

PATENT NO : 5,795,722

DATED : August 18, 1998

INVENTOR(S): Lacroix, Jean-Michel
Dunn, James M.

It is certified that error appears in the above-identified patent and that said Letters Patent is hereby corrected as shown below:

Cancell Claims 9 and 15.

Signed and Sealed this

Eighth Day of December, 1998

*Attest:*

BRUCE LEHMAN

*Attesting Officer* — Commissioner of Patents and Trademarks

SEQUENCE LISTING ( 1 ) GENERAL INFORMATION:

( i i i ) NUMBER OF SEQUENCES: 15

( 2 ) INFORMATION FOR SEQ ID NO: 1:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal ( v i ) ORIGINAL SOURCE:
        ( A ) ORGANISM: HIV-1

( i x ) FEATURE:
        ( D ) OTHER INFORMATION: amplification primer SK462 for gag ( x i ) SEQUENCE DESCRIPTION: SEQ ID NO:1:

AGTTGGAGGA CATCAAGCAG CCATGCAAAT                                                    30

( 2 ) INFORMATION FOR SEQ ID NO: 2:

( i ) SEQUENCE CHARACTERISTICS:
        ( A ) LENGTH: 27
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( i v ) ANTI-SENSE: no ( v ) FRAGMENT TYPE: internal ( v i ) ORIGINAL SOURCE:
        ( A ) ORGANISM: HIV-1

( i x ) FEATURE:
        ( D ) OTHER INFORMATION: amplification primer SK431 for gag ( x i ) SEQUENCE DESCRIPTION: SEQ ID NO:2:

TGCTATGTCA GTTCCCCTTG GTTCTCT                                                       27

( 2 ) INFORMATION FOR SEQ ID NO: 3:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( i v ) ANTI-SENSE: yes ( v ) FRAGMENT TYPE: internal ( v i ) ORIGINAL SOURCE:
        ( A ) ORGANISM: HIV-1

( i x ) FEATURE:
        ( D ) OTHER INFORMATION: amplification primer PR211 for protease
           gene ( x i ) SEQUENCE DESCRIPTION: SEQ ID NO:3:

ATCACTCTTT GGCAACGACC                                                               20

( 2 ) INFORMATION FOR SEQ ID NO: 4:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( i v ) ANTI-SENSE: yes ( v ) FRAGMENT TYPE: internal ( v i ) ORIGINAL SOURCE:
        ( A ) ORGANISM: HIV-1

( i x ) FEATURE:
        ( D ) OTHER INFORMATION: amplification primer PR281 for protease
           gene ( x i ) SEQUENCE DESCRIPTION: SEQ ID NO:4:

CAGGAGCAGA TGATACAGTA TTAG 24

( 2 ) INFORMATION FOR SEQ ID NO: 5:

( i ) SEQUENCE CHARACTERISTICS:
    ( A ) LENGTH: 25
    ( B ) TYPE: nucleic acid
    ( C ) STRANDEDNESS: single
    ( D ) TOPOLOGY: linear ( i i ) MOLECULE TYPE: other nucleic acid ( i i i ) HYPOTHETICAL: NO ( i v ) ANTI-SENSE: no ( v ) FRAGMENT TYPE: internal ( v i ) ORIGINAL SOURCE:
    ( A ) ORGANISM: HIV-1

( i x ) FEATURE:
    ( D ) OTHER INFORMATION: amplification primer PR526 for protease
      gene ( x i ) SEQUENCE DESCRIPTION: SEQ ID NO:5:

CCATTCCTGG CTTTAATTTT ACTGG 25

( 2 ) INFORMATION FOR SEQ ID NO: 6:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( i i ) MOLECULE TYPE: other nucleic acid ( i i i ) HYPOTHETICAL: NO ( i v ) ANTI-SENSE: yes ( v ) FRAGMENT TYPE: internal ( v i ) ORIGINAL SOURCE:
    ( A ) ORGANISM: Chlamydia trachomatis ( i x ) FEATURE:
    ( D ) OTHER INFORMATION: amplification primer KL1 for cryptic
      plasmid ( x i ) SEQUENCE DESCRIPTION: SEQ ID NO:6:

TCCGGAGCGA GTTACGAAGA 20

( 2 ) INFORMATION FOR SEQ ID NO: 7:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( i i ) MOLECULE TYPE: other nucleic acid ( i i i ) HYPOTHETICAL: NO ( i v ) ANTI-SENSE: no ( v ) FRAGMENT TYPE: internal ( v i ) ORIGINAL SOURCE:
    ( A ) ORGANISM: Chlamydia trachomatis ( i x ) FEATURE:
    ( D ) OTHER INFORMATION: amplification primer KL1 for cryptic plasmid ( x i ) SEQUENCE DESCRIPTION: SEQ ID NO:7:

ATTCAATGCC CGGGATTGGT                                                            20

( 2 ) INFORMATION FOR SEQ ID NO: 8:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( i v ) ANTI-SENSE: yes ( v ) FRAGMENT TYPE: internal ( v i ) ORIGINAL SOURCE:
        ( A ) ORGANISM: Chlamydia trachomatis ( i x ) FEATURE:
        ( D ) OTHER INFORMATION: amplification primer CT1431F for cryptic plasmid ( x i ) SEQUENCE DESCRIPTION: SEQ ID NO:8:

GTGCATAAAC TTCTGAGGAT                                                            20

( 2 ) INFORMATION FOR SEQ ID NO: 9:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( i v ) ANTI-SENSE: yes ( v ) FRAGMENT TYPE: internal ( v i ) ORIGINAL SOURCE:
        ( A ) ORGANISM: Chlamydia trachomatis ( i x ) FEATURE:
        ( D ) OTHER INFORMATION: amplification primer CT1548R for cryptic plasmid ( x i ) SEQUENCE DESCRIPTION: SEQ ID NO:9:

GTAAACGCTC CTCTGAAGTC                                                            20

( 2 ) INFORMATION FOR SEQ ID NO: 10:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( i v ) ANTI-SENSE: yes ( v ) FRAGMENT TYPE: internal ( v i ) ORIGINAL SOURCE:
                ( A ) ORGANISM: Chlamydia trachomatis ( i x ) FEATURE:
                ( D ) OTHER INFORMATION: amplification primer OMP314A for omp
                    gene ( x i ) SEQUENCE DESCRIPTION: SEQ ID NO:10:

TGACTTTGTT TTCGACCGYG TTTT 24

( 2 ) INFORMATION FOR SEQ ID NO: 11:

( i ) SEQUENCE CHARACTERISTICS:
                ( A ) LENGTH: 23
                ( B ) TYPE: nucleic acid
                ( C ) STRANDEDNESS: single
                ( D ) TOPOLOGY: linear ( i i ) MOLECULE TYPE: other nucleic acid ( i i i ) HYPOTHETICAL: NO ( i v ) ANTI-SENSE: no ( v ) FRAGMENT TYPE: internal ( v i ) ORIGINAL SOURCE:
                ( A ) ORGANISM: Chlamydia trachomatis ( i x ) FEATURE:
                ( D ) OTHER INFORMATION: amplification primer OMP711 for omp
                    gene ( x i ) SEQUENCE DESCRIPTION: SEQ ID NO:11:

CATCCACATT CCCASARAGC TGC 23

( 2 ) INFORMATION FOR SEQ ID NO: 12:

( i ) SEQUENCE CHARACTERISTICS:
                ( A ) LENGTH: 25
                ( B ) TYPE: nucleic acid
                ( C ) STRANDEDNESS: single
                ( D ) TOPOLOGY: linear ( i i ) MOLECULE TYPE: other nucleic acid ( i i i ) HYPOTHETICAL: NO ( i v ) ANTI-SENSE: yes ( v ) FRAGMENT TYPE: internal ( v i ) ORIGINAL SOURCE:
                ( A ) ORGANISM: Chlamydia trachomatis ( i x ) FEATURE:
                ( D ) OTHER INFORMATION: amplification primer MF21 for omp gene ( x i ) SEQUENCE DESCRIPTION: SEQ ID NO:12:

CCGACCGCGT CTTGAAAACA GATGT 25

( 2 ) INFORMATION FOR SEQ ID NO: 13:

( i ) SEQUENCE CHARACTERISTICS:
                ( A ) LENGTH: 21
                ( B ) TYPE: nucleic acid
                ( C ) STRANDEDNESS: single
                ( D ) TOPOLOGY: linear ( i i ) MOLECULE TYPE: other nucleic acid ( i i i ) HYPOTHETICAL: NO (iv) ANTI-SENSE: no (v) FRAGMENT TYPE: internal (vi) ORIGINAL SOURCE:
(A) ORGANISM: Chlamydia trachomatis (ix) FEATURE:
(D) OTHER INFORMATION: amplification primer MB22 for omp gene (xi) SEQUENCE DESCRIPTION: SEQ ID NO:13:

CACCCACATT CCCAGAGAGC T                                      21

(2) INFORMATION FOR SEQ ID NO: 14:

(i) SEQUENCE CHARACTERISTICS:
(A) LENGTH: 21
(B) TYPE: nucleic acid
(C) STRANDEDNESS: single
(D) TOPOLOGY: linear (ii) MOLECULE TYPE: other nucleic acid (iii) HYPOTHETICAL: NO (iv) ANTI-SENSE: yes (v) FRAGMENT TYPE: internal (vi) ORIGINAL SOURCE:
(A) ORGANISM: Chlamydia trachomatis (ix) FEATURE:
(D) OTHER INFORMATION: amplification primer MVF3 for omp gene (xi) SEQUENCE DESCRIPTION: SEQ ID NO:14:

CGTGCAGCTT TGTGGGAATG T                                      21

(2) INFORMATION FOR SEQ ID NO: 15:

(i) SEQUENCE CHARACTERISTICS:
(A) LENGTH: 24
(B) TYPE: nucleic acid
(C) STRANDEDNESS: single
(D) TOPOLOGY: linear (ii) MOLECULE TYPE: other nucleic acid (iii) HYPOTHETICAL: NO (iv) ANTI-SENSE: no (v) FRAGMENT TYPE: internal (vi) ORIGINAL SOURCE:
(A) ORGANISM: Chlamydia trachomatis (ix) FEATURE:
(D) OTHER INFORMATION: amplification primer MB4 for omp gene (xi) SEQUENCE DESCRIPTION: SEQ ID NO:15:

CTAGATTTCA TCTTGTTCAA TTGC                                   24